(12) United States Patent
Farooqui

(10) Patent No.: US 7,437,785 B2
(45) Date of Patent: Oct. 21, 2008

(54) DRIVE SYSTEM FOR IMAGING DEVICE

(75) Inventor: Asghar Ali Farooqui, Bangalore (IN)

(73) Assignee: General Electric Company, Schenectady, NY (US)

( * ) Notice: Subject to any disclaimer, the term of this patent is extended or adjusted under 35 U.S.C. 154(b) by 327 days.

(21) Appl. No.: 11/278,254

(22) Filed: Mar. 31, 2006

(65) Prior Publication Data
US 2007/0226906 A1 Oct. 4, 2007

(51) Int. Cl.
*A61G 7/14* (2006.01)
(52) U.S. Cl. .................... 5/601; 5/81.1 HS; 378/209
(58) Field of Classification Search .......... 5/81.1 HS, 5/601; 378/209
See application file for complete search history.

(56) References Cited

U.S. PATENT DOCUMENTS

| | | | | |
|---|---|---|---|---|
| 3,588,500 | A * | 6/1971 | Koerner | 5/601 |
| 4,568,071 | A * | 2/1986 | Rice | 5/601 |
| 4,984,774 | A * | 1/1991 | Zupancic et al. | 5/601 |
| 5,013,018 | A | 5/1991 | Siczek | |
| 5,207,115 | A * | 5/1993 | Takei | 74/479.01 |
| 5,272,776 | A * | 12/1993 | Kitamura | 5/601 |
| 6,240,582 | B1 * | 6/2001 | Reinke | 5/601 |
| 6,363,555 | B1 * | 4/2002 | LaRose | 5/600 |
| 6,668,403 | B2 * | 12/2003 | Seufert | 5/601 |
| 6,955,464 | B1 | 10/2005 | Tybinkowski | |
| 7,103,931 | B2 * | 9/2006 | Somasundaram et al. | 5/601 |

* cited by examiner

*Primary Examiner*—Michael Trettel

(57) ABSTRACT

A drive system for an imaging device is provided. The drive system comprises a table assembly for engaging and supporting a patient and a driving system for moving the table assembly. The driving system can be directly coupled to the table assembly. The table assembly comprises a carrier that engages and supports a patient and at least two elongated rails placed beneath the carrier and extending between the opposing sides of the table assembly. The driving system for moving the table assembly comprises at least one double end shaft motor, at least one belt coupled to the double end shaft motor via a coupling device and at least one pair of timer pulleys coupled to the belt. Further, each timer pulley is directly coupled to a feedback device at a first end and a brake device at a second end.

17 Claims, 4 Drawing Sheets

DRIVE SYSTEM FOR IMAGING DEVICE

FIELD OF INVENTION

This invention relates generally to an imaging device and more particularly to a patient positioning system in an imaging device.

BACKGROUND OF THE INVENTION

Patient positioning systems are used by imaging devices to position patients with respect to an imaging system of the imaging device. For example, computed tomography (CT) imaging systems typically include a patient positioning system including a table upon which the patient lies and a drive system to move the table (and hence the patient) as the patient is scanned by the CT imaging system. A conventional drive system in an imaging device comprises a driving system to convert a rotary motion to a linear motion. The driving system uses one of a screw drive mechanism and a friction drive mechanism to convert a rotary motion to the linear motion. The screw drive mechanism comprises a driving screw and one or more linear guides. The linear guides are linear motion bearings that bear loads to guide the linear motion. The driving system further comprises a motor to create the rotary motion to drive the screw drive mechanism. The motor can be a single end shaft motor comprising a front bearing. Due to overhang leverage and cantilever behavior of the single end shaft motor, the driving system overloads the front bearing. The overload can lead to overheating and failure of the front bearing.

The screw drive mechanism has an issue of friction and wear. Moreover, the single end shaft motor used in the screw drive system has an issue of over hang load, which cannot be resolved unless a higher size motor is used. The primary limitation in the screw drive mechanism is that, the alignment between the linear guides and the driving screw is critical to the quality (CTQ). The alignment is taxing to manufacturing as well as production teams. Hence there exists a need for adapting an efficient and positive drive system in the imaging device.

SUMMARY OF THE INVENTION

The above-mentioned shortcomings, disadvantages and problems are addressed herein which will be understood by reading and understanding the following specification.

In an embodiment, the invention provides a drive system for an imaging device. The drive system includes a table assembly and a driving system. The table assembly engages and supports a patient. The driving system moves the table assembly, and includes a double end shaft motor coupled to the table assembly.

In another embodiment, the invention provides a simple, compact, reliable and accurate drive system for an imaging device. The drive system comprises a table assembly and a driving system. The driving system is coupled to the table assembly. The table assembly comprises a carrier and two or more elongated rails placed beneath the carrier. The driving system comprises one or more double end shaft motors. A single double end shaft motor is used along with other support accessories in a simple and effective way. The driving system further comprises one or more belts driven by the double end shaft motor. The double end shaft motor is coupled to the belt by means of a coupling device. Two or more timer pulleys are mounted on the double end shaft motor to drive the belt. The timer pulleys are positive drive elements that are coupled to a feedback device and a brake device at each end. The feedback device provides a greater positioning accuracy. The brake device provides a better safety and imparts a robust design feature to the driving system. The driving system imparts a similar function as a screw drive mechanism with an increased flexibility and an enhanced motor life.

In another embodiment, the invention provides a patient positioning system. The patient positioning system comprises a table assembly and a driving system for driving the table assembly. The table assembly comprises a carrier and two or more elongated rails. The carrier is used for engaging and supporting a patient. The elongated rails are placed beneath the carrier and extend between the opposing sides of the table assembly.

The driving system comprises one or more belts. The belt is coupled to the carrier of the table assembly. The driving system further comprises one or more double end shaft motors. The belt is coupled to the double end shaft motor by means of a coupling device. Multiple timer pulleys are mounted on the double end shaft motor, which in turn are configured to drive the belt. Each timer pulley is further coupled to a feedback device at a first end and a brake device at a second end.

Systems and methods of varying scope are described herein. In addition to the aspects and advantages described in this summary, further aspects and advantages will become apparent by reference to the drawings and with reference to the detailed description that follows.

DETAILED DESCRIPTION OF THE INVENTION

In the following detailed description, reference is made to the accompanying drawings that form a part hereof, and in which is shown by way of illustration specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

In various embodiments of the invention, a drive system for an imaging device and an imaging device using a drive system are described. However, the embodiments are not limited and may be implemented in connection with different applications. The application of the invention can be extended to other areas, for example positioning devices. The invention provides a broad concept of a rotary motion translating to a linear motion application, which can be adapted in a similar positioning system. The design can be carried further and implemented in various forms and specifications.

The drive system for an imaging device provided in various embodiments of the invention comprises a table assembly and a driving system. The driving system can be directly coupled to the table assembly. The table assembly can comprise a carrier and two or more elongated rails. The carrier can be used for engaging and supporting a patient. The elongated rails can be provided at the bottom side of the carrier and can extend between the opposing sides of the table assembly. The elongated rails are provided for co-operation during longitudinal movement of the carrier. The driving system comprises one or more double end shaft motors comprising shafts that extend outwardly in opposite directions. One or more timer pulleys can be mounted on each end of the double end shaft motor. One or more belts can extend over the timer pulleys. The belts can be coupled to the double end shaft motor through a coupling device. The belt can also be coupled to the carrier of the table assembly through a clamp.

Energization of the double end shaft motor imparts driving motion to the timer pulleys causing displacement of the belt. The belts drive the carrier of the table assembly simultaneously with elongated rails along the complete linear length. The timer pulleys can be directly coupled to a feedback device at a first end and a brake device at a second end. The revolution-per-minute (RPM) of the double end shaft motor is in close loop with the timer pulley through the feedback device. The feedback device and brake device when directly coupled to the timer pulley provide a robust and reliable design compared to an indirect means of coupling.

Figure 1:
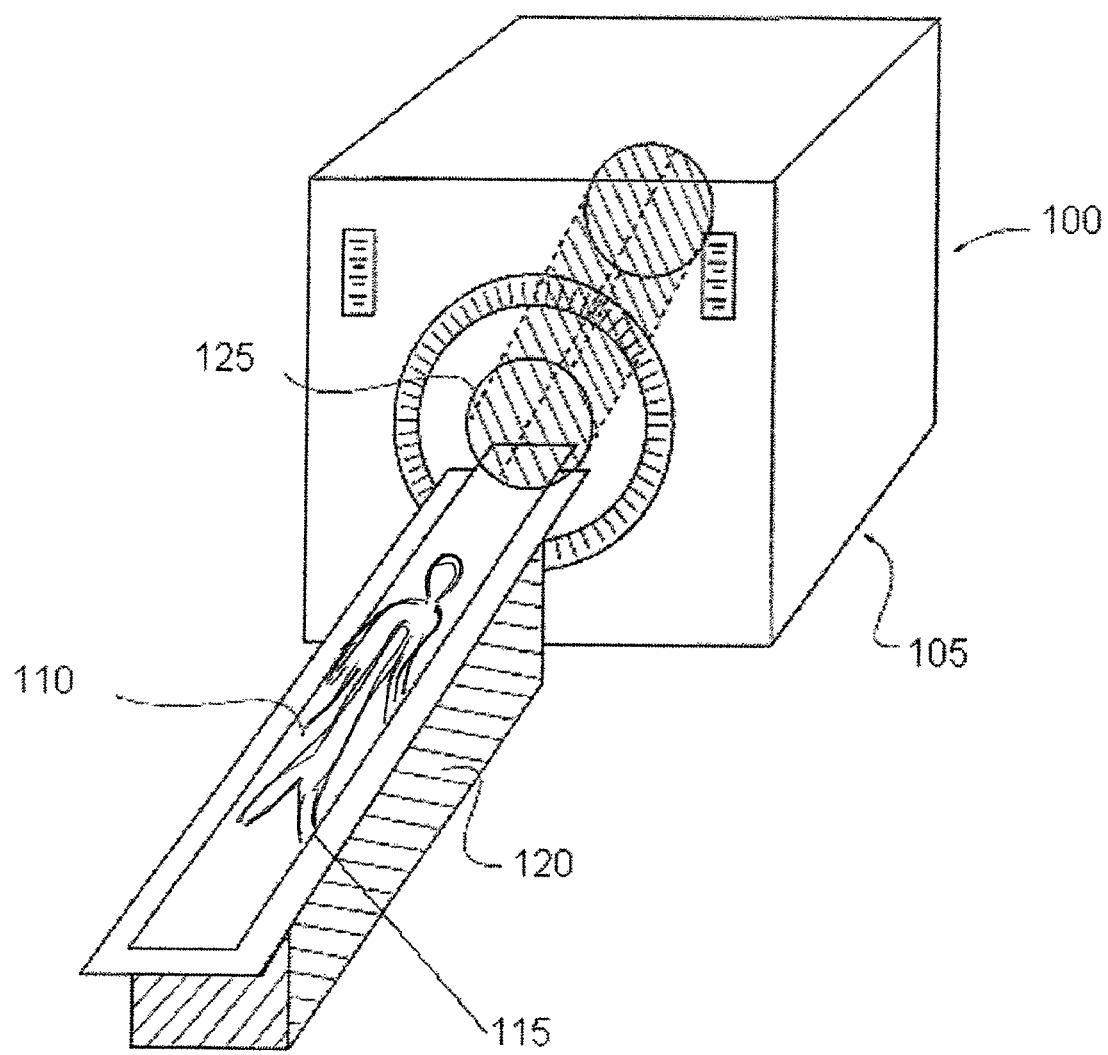
FIG. 1 shows a schematic diagram of an example of an imaging device in an embodiment of the invention.

FIG. 1 shows a schematic diagram of an example of an imaging device 100. The imaging device 100 can be one of a computed tomography device, a positron emission tomography device, a magnetic resonance imaging device, an ultrasound-imaging device and an X-ray device. One skilled in the art will however appreciate that, the examples of the imaging device are not limited to the examples mentioned above and the invention shall have full scope of the claims.

The imaging device 100 comprises an imaging gantry 105. The imaging gantry 105 includes a tunnel 125 for receiving a patient 110. A table assembly 115 is provided for engaging and supporting the patient 110. A driving system 120 is provided for moving the table assembly 115, which is received in the tunnel 125 of the imaging device 100.

Figure 2:
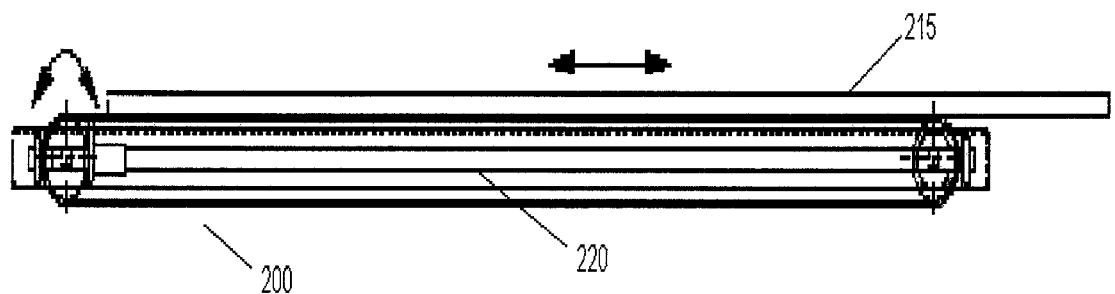
FIG. 2 shows a schematic diagram of a side view of a drive system for the imaging device in one embodiment of the invention.

FIG. 2 shows a schematic diagram of a side view of a drive system 200 for the imaging device 100. The drive system 200 comprises a table assembly 215 and a driving system 220. The driving system 220 can be directly coupled to the table assembly 215.

Figure 3:
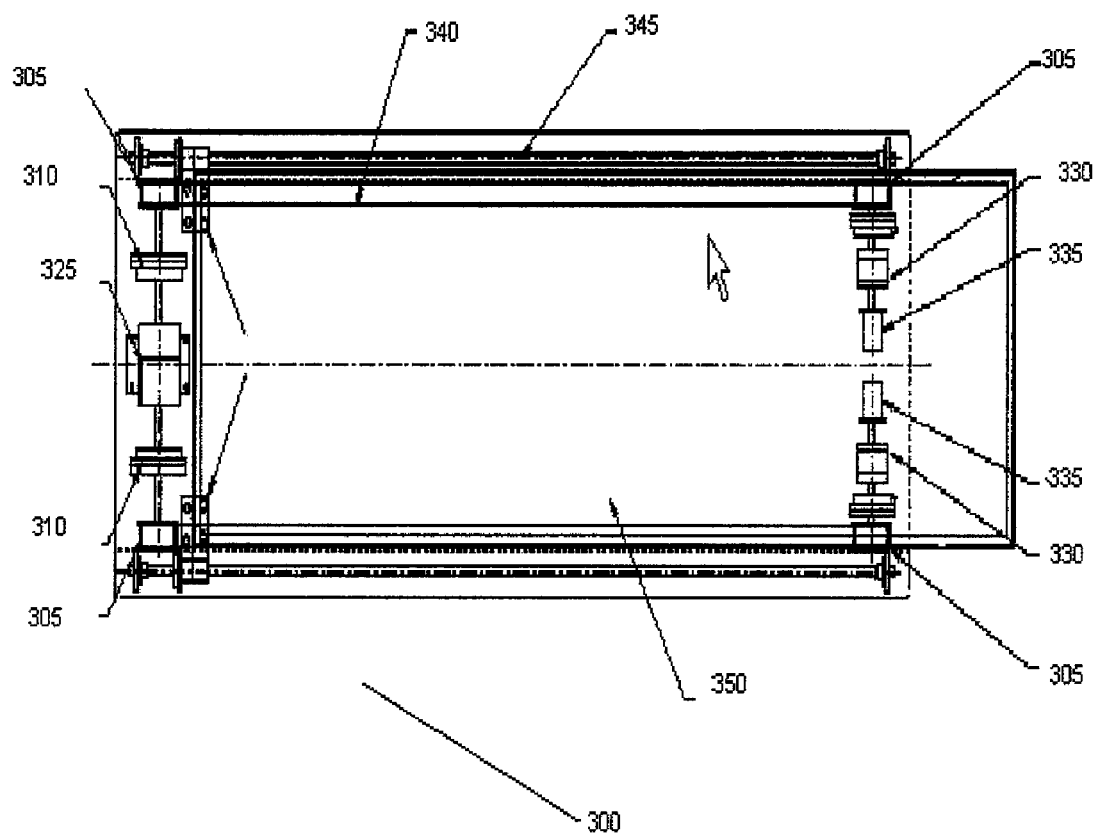
FIG. 3 shows a schematic diagram of a top view of the drive system for the imaging device in another embodiment of the invention.

FIG. 3 shows a schematic diagram of a top view of the drive system 200. The table assembly 215 of the drive system 200 can comprise a carrier 350 that engages and supports a patient 110. The table assembly 215 can also comprise structural members such as elongated rails 345 for enabling the movement of the carrier 350 along a horizontal axis. The carrier 350 is slidably mounted on the elongated rails 345 of the table assembly 215. The elongated rails 345 can be made from a relatively lightweight and inexpensive, yet rigid and strong material such as aluminum. The elongated rails 345 can be identical and can be manufactured through an extrusion process to reduce costs. Among the other advantages, the use of extruded elongated rails 345 greatly simplifies the design, assembly and overall cost of the table assembly 215.

The driving system 220 for moving the table assembly 215 is a rotary-to-linear motion converter. The driving system 220 can comprise one or more double end shaft motors 325. The double end shaft motor 325 can be a stepper or a servo motor. Operation of the double end shaft motor 325 causes a linear motion of the table assembly 215. One or more belts 340 for example, tooth belt can be coupled to the double end shaft motor 325 via a coupling device 310. The coupling device 310 provides smoother engagement and eliminates chatter. Further the coupling device 310 can be configured to be an electro-mechanical clutch.

The driving system 220 can further comprise multiple timer pulleys 305 rotatably placed beneath the table assembly 215 adjacent to a rear end of the table assembly 215. Operation of the double end shaft motor 325 causes rotation of the timer pulley 305. The timer pulleys 305 drive the belt 340 extending between the timer pulleys 305. The belt 340 in turn secures the carrier 350 of the table assembly 215 through a clamp. Therefore, the rotation of the timer pulleys 305 causes a linear movement of the carrier 350 and the table assembly 215.

Each timer pulley 305 can be directly coupled to a feedback device 335 at a first end. The feedback device 335 is a sensor assembly providing an indication of an absolute position of the carrier 350 with respect to the table assembly 215. The sensor assembly comprises a magnet secured to the carrier 350 and a magnetic absolute linear position sensor secured to one of the elongated rails 345 of the table assembly 215. The relative position of the carrier 350 with respect to the magnetic absolute linear position sensor of the elongated rails 345 can be determined from the output signal provided by the magnetic absolute linear position sensor. The feedback device 335 can be configured to be an encoder. More particularly, the feedback device 335 can be configured to be an absolute encoder.

The timer pulley 305 can also be coupled to a brake device 330 at a second end. The brake device can be a positive clamping device. The brake device ensures that the carrier position is not disturbed after the carrier is positioned at a predetermined position. Further, the brake device 330 can configured to be an electro-mechanical brake.

Figure 4:
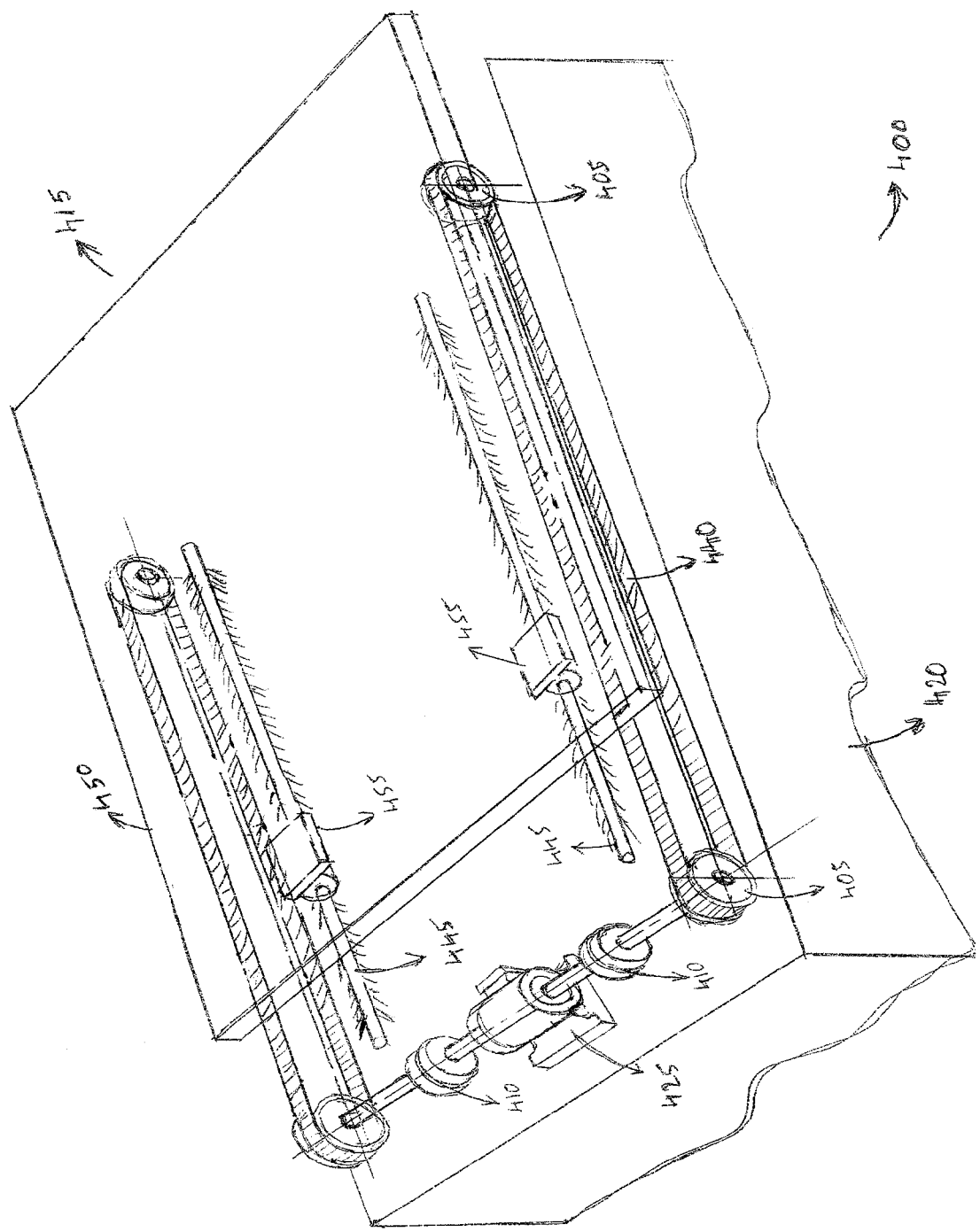
FIG. 4 shows a schematic diagram of a drive system in another embodiment of the invention.

Further, FIG. 4 shows a schematic diagram of a drive system 400 in another embodiment of the invention. The drive system 400 can comprise a driving system 420 and a table assembly 415. The table assembly 415 can comprise a carrier 450 for carrying the patient 110. The table assembly 415 can further comprise at least a pair of elongated rails 445 running beneath the carrier 450 and extending between the opposing sides of the table assembly 415. A linear guide 455 can be mounted on each of the elongated rails 445 in order to guide the linear motion of the carrier 450. The driving system 420 for driving the table assembly 415 comprises at least one double end shaft motor 425. The double end shaft motor comprises two shafts extending through the double end shaft motor 425. Each shaft of the double end shaft motor 425 is coupled to at least one timer pulley 405 through a coupling device 410 such as an electro-mechanical clutch. Further, each timer pulleys 405 can be directly coupled to a feedback device such as an absolute encoder at a first end and a brake device such as an electro-mechanical brake at a second end. At least one belt 440 can be coupled to the timer pulleys 405. The belt 440 can also be clamped to the carrier 450 of the table assembly 415 in order to engage and move the patient 110.

In yet another embodiment of the invention a patient positioning system is provided. The patient positioning system can comprise a table assembly 415 for engaging and supporting a patient 110. The table assembly 415 can comprise a carrier 450 and two or more elongated rails 445. The carrier 450 is used for engaging and supporting the patient 110. The elongated rails 445 can be placed beneath the carrier 450. The elongated rails 445 can extend between the opposing sides of the table assembly 415. The patient positioning system can further comprise a driving system 420 for driving the table assembly 415. The driving system 420 can comprise one or more double end shaft motors 425 for driving the table assembly 415. One or more belts 440 can be coupled to the double end shaft motor 425 by means of a coupling device 410. The belts 440 can be directly coupled to the carrier 450 of the table assembly 415. Multiple timer pulleys 405 can be mounted on the double end shaft motor 425 to drive the belt 440. Further, the timer pulleys 405 can directly be coupled to the feedback device 335 at a first end and the brake device 330 at a second end.

Some of the advantages of the drive system 400 provided in various embodiments of the invention include a higher fatigue life of the double end shaft motor 425 and the belt 440 with a significantly decreased wear and tear, in comparison to conventional drive systems such as those including screw drives. The drive system 400 inherently takes care of the overhang issues. The double end shaft motor 425 nullifies the overhang effect as equal and opposite force act on both the ends of the double end shaft motor 425. The rating of the double end shaft motor 425 can be lower than the rating of the single end shaft motor used in a conventional screw drive mechanism.

Components such as belts 440 and timer pulleys 405 used in the drive system 400 are easily available at a nominal cost. Critical components used in the drive system 400 of the invention are bought out components and hence replacement or repair cost is reduced significantly. Therefore, the cost savings are reduced greatly when compared to a screw drive mechanism.

The manufacturing and production of the drive system 400 is simple when compared to the conventional screw drive system. The drive system 400 requires less assembly time and can be accommodated easily due to the flexibility of the belt 440 used in the drive system 400. Therefore the manufacturing, assembling, transport and handling of the drive system 400 are simple, cheap and reliable.

The noise generated from the drive system 400 provided is less than that of conventional screw drive systems, and is approximately zero in the context of its application in various types of imaging devices. The drive system 400 is not CTQ because of the flexible nature of the belt 440 used and hence the invention provides a positive drive system 400 and not a friction based drive system.

One skilled in the art shall however appreciate that, the advantages of the drive system 400 provided in various embodiments of the invention are not limited to the examples given above and all such advantages are within the scope of the invention.

What is claimed is:

1. A drive system for an imaging device comprising:
a table assembly for engaging and supporting a patient; and
a driving system for moving the table assembly, wherein the driving system includes a double end shaft motor coupled to the table assembly, and further comprises:
at least one belt coupled to the double end shaft motor via a coupling device; and
at least a pair of timer pulleys coupled to the belt, each timer pulley being coupled to a feedback device at a first end and a brake device at a second end.

2. The drive system of claim 1, wherein the belt is a tooth belt, and the belt is directly coupled to a carrier of the table assembly.

3. The drive system of claim 1, wherein the brake device is configured to be an electro-mechanical brake.

4. The drive system of claim 1, wherein the feedback device is configured to be an absolute encoder.

5. The drive system of claim 1, wherein the coupling device is configured to be an electro-mechanical clutch.

6. A drive system for an imaging device, the drive system comprising:
a carrier that engages and supports a patient; and
a driving system comprising,
at least one double end shaft motor;
at least one belt extending through the carrier and directly coupled to the carrier; and
at least a pair of timer pulleys coupled to the belt, each timer pulley being directly coupled to a feedback device at a first end and a brake device at a second end.

7. The drive system of claim 6, further comprising at least two elongated rails placed beneath the carrier and extending between opposing sides of the table assembly.

8. The drive system of claim 6, further comprising a coupling device, wherein the belt is coupled to the double end shaft motor through the coupling device.

9. The drive system of claim 8, wherein the coupling device is configured to be an electro-mechanical clutch.

10. The drive system of claim 6, wherein the brake device is configured to be an electro-mechanical brake.

11. The drive system of claim 6, wherein the feedback device is configured to be an absolute encoder.

12. The drive system of claim 6, wherein the imaging device is one of a computed tomography device, a positron emission tomography device, a magnetic resonance imaging device, an ultrasound imaging device and an X-ray device.

13. A patient positioning system comprising:
a table assembly for engaging and supporting a patient, the table assembly comprising,
a carrier for engaging and supporting the patient and at least two elongated rails placed beneath the carrier, extending between opposing sides of the table assembly; and
a driving system for driving the table assembly comprising,
at least one belt directly coupled to the carrier;
at least one double end shaft motor; and
at least a pair of timer pulleys coupled to the belt wherein each timer pulley is directly coupled to a feedback device at a first end and a brake device at a second end.

14. The patient positioning system of claim 13, further comprising a coupling device, wherein the belt is coupled to the double end shaft motor through the coupling device.

15. The patient positioning system of claim 14, wherein the coupling device is configured to be an electro-mechanical clutch.

16. The patient positioning system of claim 13, wherein the brake device is configured to be an electro-mechanical brake.

17. The patient positioning system of claim 13, wherein the feedback device is configured to be an absolute encoder.

* * * * *